United States Patent [19]

Sinya

[11] Patent Number: 5,243,401
[45] Date of Patent: Sep. 7, 1993

[54] FLUORESCENT IMAGE DENSITOMETER OF FLYING SPOT SYSTEM

[75] Inventor: Kazunari Sinya, Takatuki, Japan

[73] Assignee: Shimadzu Corporation, Kyoto, Japan

[21] Appl. No.: 827,219

[22] Filed: Jan. 30, 1992

[30] Foreign Application Priority Data

Jan. 31, 1991 [JP] Japan .................................. 3-32508

[51] Int. Cl.$^5$ .......................................... G01N 21/64
[52] U.S. Cl. ................................. 356/318; 250/458.1; 356/243
[58] Field of Search ............... 356/243, 317, 318, 417; 250/458.1, 459.1

[56] References Cited

U.S. PATENT DOCUMENTS

| | | | |
|---|---|---|---|
| 3,936,190 | 2/1976 | Ohnishi et al. | 250/458.1 X |
| 4,631,581 | 12/1986 | Carlsson | 356/318 X |
| 4,662,745 | 5/1987 | Zupanick et al. | 356/243 |
| 4,762,412 | 8/1988 | Ohkubo et al. | 356/319 |
| 4,881,812 | 11/1989 | Ohkubo et al. | 356/417 X |

*Primary Examiner*—Vincent P. McGraw
*Attorney, Agent, or Firm*—Nikaido, Marmelstein, Murray & Oram

[57] ABSTRACT

A two-dimensional fluorescent densitometry for measuring a specimen plate having a specimen spot such as phospholipide two-dimensionally developed and fluorescent-labelled on a TLC plate. The densitometer comprises an excitation optical system for scanning a measuring plate with an excitation light beam, a fluorescence detection system for detecting a fluorescence from the measuring plate, a correction table for storing fluorescent data together with positional information in a scanning direction on the measuring plate, and an arithmetic section for dividing fluorescence detection data by fluorescent data at the same position in the scanning direction on the measuring plate stored in the correction table.

3 Claims, 5 Drawing Sheets

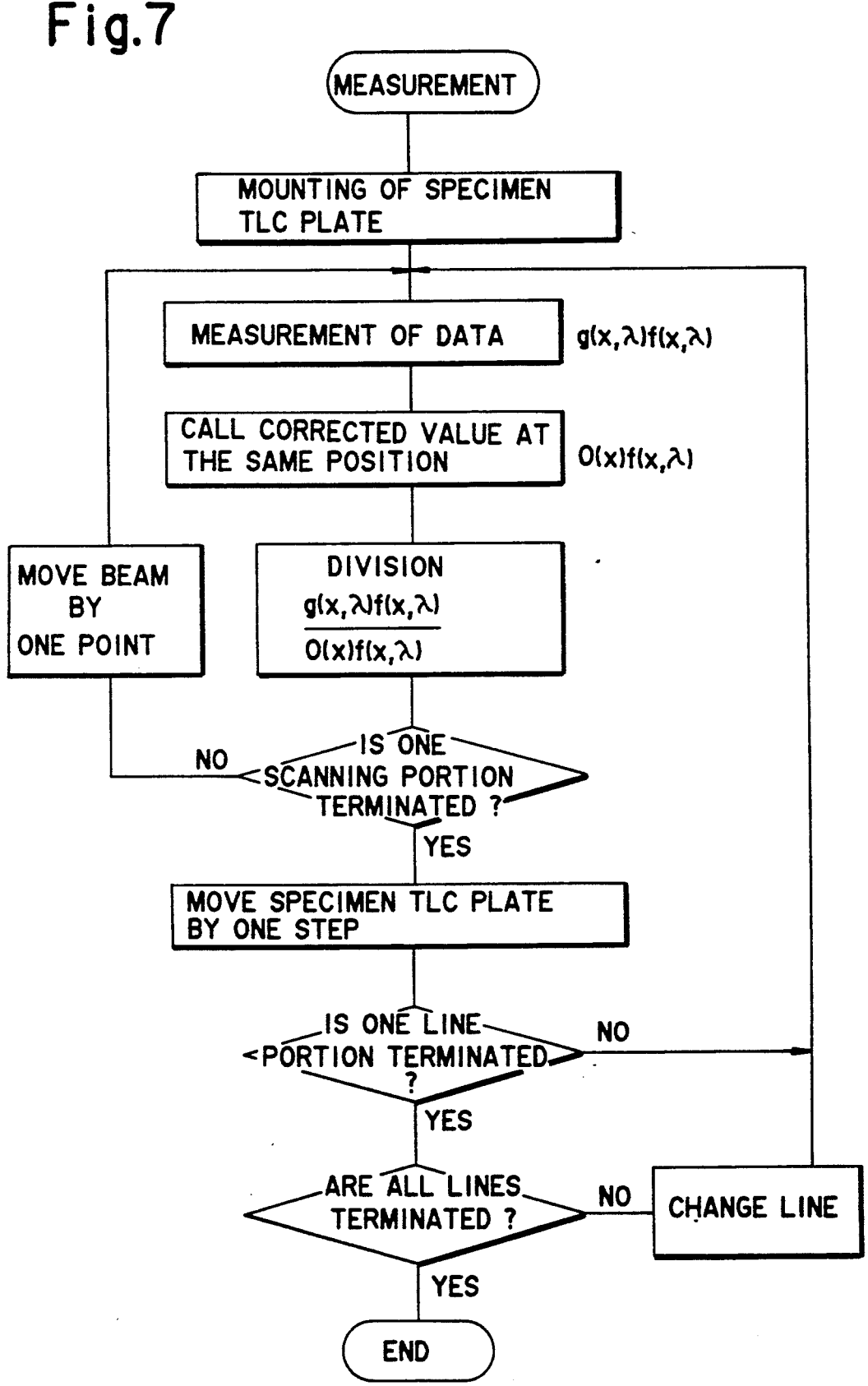

FLUORESCENT IMAGE DENSITOMETER OF FLYING SPOT SYSTEM

BACKGROUND OF THE INVENTION

1. Field of the Invention

The present invention relates to a two-dimensional fluorescent densitometry for measuring a specimen plate having a specimen spot such as phospholipide two-dimensionally developed and fluorescent-labelled on a TLC plate (thin film chromatography plate).

2. Description of the Prior Art

As a two-dimensional densitometer for measuring a specimen developed on the TLC plate, there is a densitometer of flying spot system which scans a measuring light in a reciprocating direction on the TLC plate and moves the TLC plate in a direction perpendicularly intersecting thereto to effect measurement.

The conventional densitometry measures the absorbancy from the reflective light and transmissive light of the measuring light caused by the specimen.

According to the flying spot system, a luminous flux is limited by a helical slit Sr whose distance from the center uniformly changes and a fixed slit Sfix extending radially of a slit disk 24 having said helical slit Sr and combined with said helical slit Sr, and the luminous flux on a specimen surface is laterally shaken by the reciprocating rotational motion of the helical slit Sr. In the case where the luminous flux is shaken on the specimen surface, the luminous flux has a so-called locality in which intensity differs with locations in the scanning direction. It is considered that the luminous flux has the locality due to the causes such as unevenness of width of a groove hole of the helical slit Sr, individuality of the optical system, particularly distribution of intensities of light irradiated on the fixed slit Sfix or changes in quantity of incident light to a detector due to an inclination of a light path when the luminous flux is shaken laterally.

In such a locality as described, it is possible for the densitometry for measuring the absorbancy of reflective light or transmissive light from the specimen to extract a part of the irradiated light by a half mirror or the like to monitor it.

As a densitometry, there can be considered a fluorescent mapping densitometer for fluorescent-labelling a specimen component developed on a specimen plate. The specimen component is fluorescent-labelled, and the specimen component is excited by an excitation light to excite the specimen component of which fluorescence is measured, whereby measurement with high sensitivity as compared with the conventional method for measuring the absorbancy can be carried out. However, the fluorescent mapping densitometry cannot correct the locality by the conventional system.

SUMMARY OF THE INVENTION

It is an object of the present invention to correct the locality in realizing the fluorescent mapping densitometry of the flying spot system.

According to one aspect of the present invention there is provided a fluorescent image densitometer of flying spot system comprising an excitation optical system for scanning and irradiating a measuring plate with an excitation light beam; a fluorescence detection system for detecting a fluorescence from an excitation light irradiation position of the measuring plate; a correction table for storing fluorescent data, measured with a plate uniformly applied with a fluorescent agent at least within a range of excitation light scanning mounted as the measuring plate, together with information of a position in a scanning direction on the measuring plate; and an arithmetic section for dividing fluorescence detection data measured with a specimen plate mounted as the measuring plate by fluorescent data at the same position in the scanning direction on the measuring plate stored in said correction table.

BRIEF DESCRIPTION OF THE DRAWINGS

FIG. 7 is a flow chart showing the measurement of specimen.

DETAILED DESCRIPTION OF THE PREFERRED EMBODIMENTS

Figure 1:
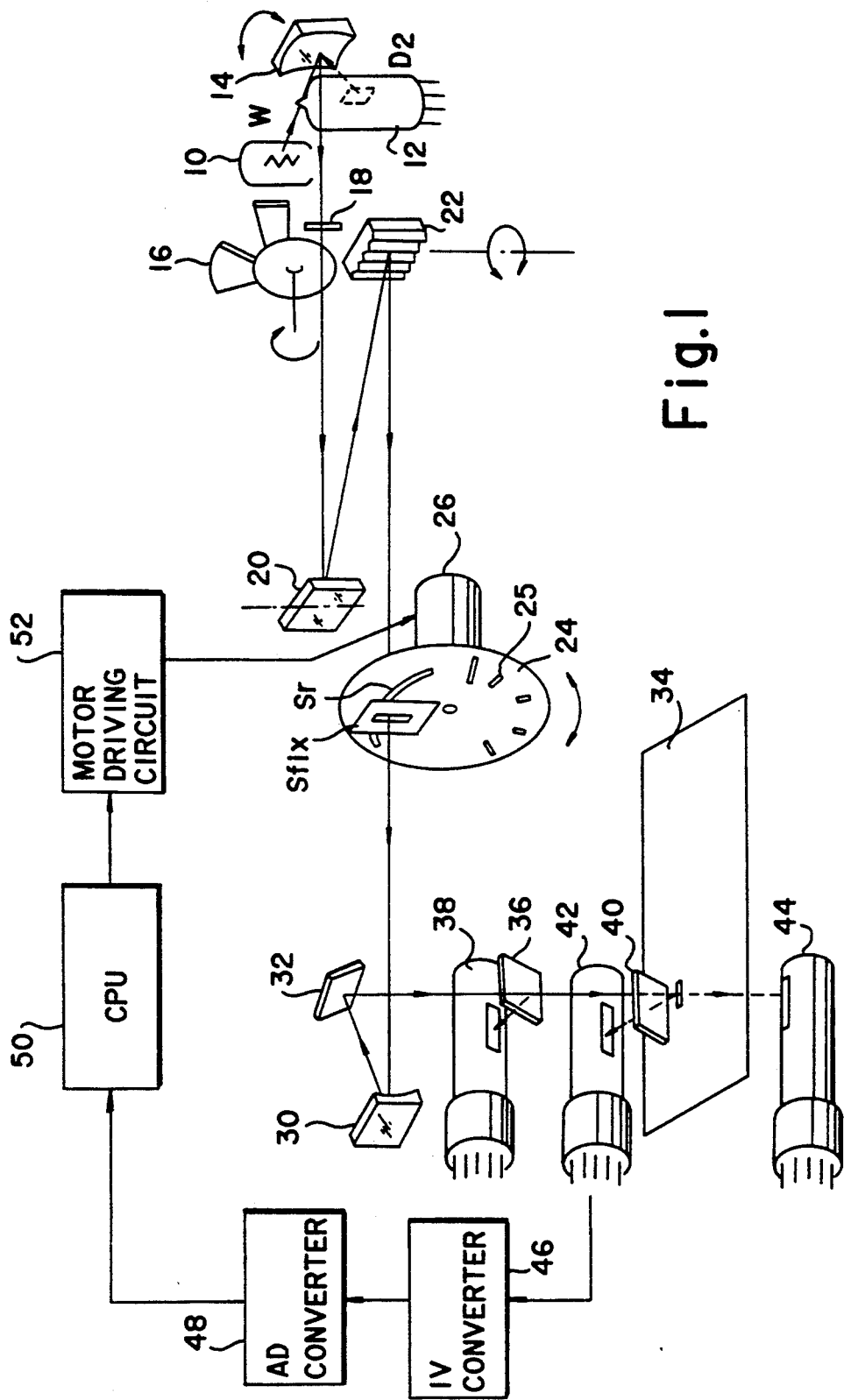
FIG. 1 is a structure view showing one embodiment.

FIG. 1 shows one embodiment.

Reference numeral 10 designates a tungsten halogen lamp and 12 designates a heavy hydrogen lamp. There are provided two kinds of lamps as light sources. Reference numeral 14 designates a light-source switching mirror, which is used to use light from either lamp 10 or 12 as excitation light. Reference numeral 16 designates a cut filter. A filter for causing light of an excitation light component to be transmitted is inserted into a light path. Reference numeral 18 designates an inlet slit of a spectroscope; 20, a collimeter of a spectroscope; and 22, a diffraction grating. Outlet slits of a spectroscope are a helical slit Sr and a fixed slit Sfix. The helical slit Sr is in the form of a disk 24, the helical slit Sr being designed to have a shape in which the distance from the center of the disk 24 is monotonously changed. The disk 24 is formed with several slits 25 whose sizes of holes are different other than the helical slit Sr. These fixed slits 25 are used with the disk 24 stopped in the case of measurement with an irradiation beam fixed. When the flying spot system is employed, the disk 24 is rotatively driven in the reciprocating direction within the range in which the excitation light transmits through the helical slit Sr. Reference numeral 26 designates a stepping motor for driving the disk 24. Combined with the helical slit Sr is the fixed slit Sfix extending in a radial direction of the disk 24.

The excitation light from the spectroscope is irradiated on a measuring plate 34 via a concave mirror 30 and a plane mirror 32. A crystal window plate 36 is arranged as a half mirror in an excitation-light light path extending from the mirror 32 to the measuring plate 34. A art of excitation light extracted by the half mirror 36 is monitored by a monitoring photoelectron multiplication tube 38. A fluorescence photoelectron multiplication tube 42 is arranged through a filter 40 for causing fluorescence to be transmitted to shield excitation light in order that excitation light is incident upon the measuring plate 34 and the fluorescence is measured from the excitation portion. A transmission photoelectron multiplication tube 44 is also arranged on the back surface of the measuring plate in order to measure an intensity of transmission light at the irradiation position of the measuring plate 34.

A detection output of the photoelectron multiplication tube 42 for measuring the fluorescence is converted into a voltage value by a 1-V converter 46 and further converted into a digital signal by an AD converter 48, after which it is incorporated into a CPU 50 for data processing. The CPU 50 also controls a driving circuit 52 for the stepping motor 26.

Figure 2:
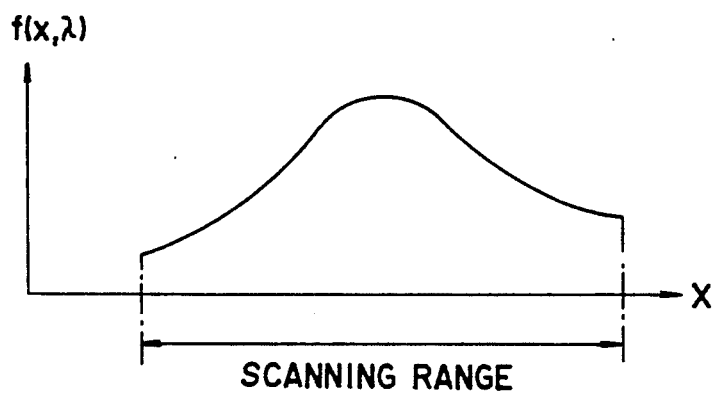
FIG. 2 is a view showing locality of excitation light intensity in the scanning of luminous flux.

The excitation light for irradiating the measuring plate 34 has a locality. The locality is a function f (x, λ) between the position x in the scanning direction of the irradiation beam and the excitation-light wavelength λ. The TLC plate with a fluorescent agent is mounted as the measuring plate 34. Let σ(λ) be the fluorescent intensity when excitation is made with light of unit intensity. Then, when the TLC plate is excited with light of intensity f (x, λ) having the locality as shown in FIG. 2, the fluorescent intensity is σ(λ) f (x, λ), because the proportional relation exists between the fluorescent intensity and the excitation-light intensity according to the formula of quantization efficiency.

Accordingly, the σ(λ) f (x, λ) is held in the correction of locality, which is divided by the fluorescent intensity σ(λ) f (x, λ). Then, 1 is obtained everywhere on the TLC plate with a fluorescent agent to obtain a uniform fluorescent intensity.

Figure 3:
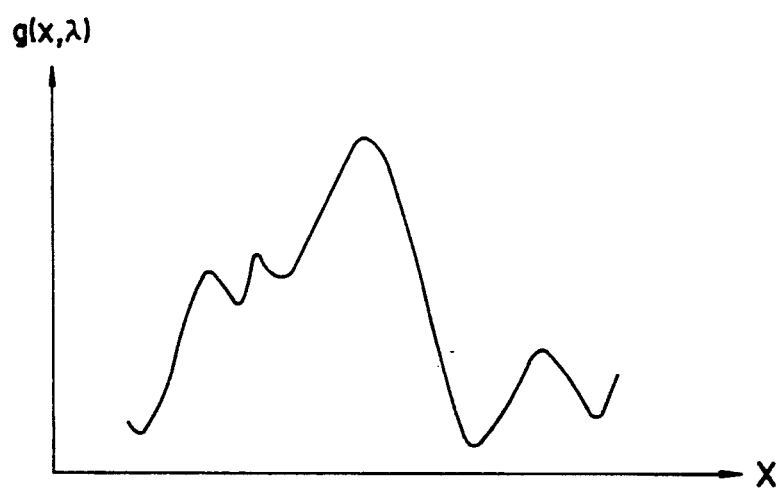
FIG. 3 is a view showing a fluorescence intensity when a specimen plate is measured.

Next, in the case where a specimen plate is mounted as the measuring plate, let g (x, λ) be the fluorescence when excitation is made with light of unit intensity. Then, the g (x, λ) is as shown in FIG. 3, for example. A signal obtained by a densitometer is g (x, λ) f (x, λ) due to the locality of excitation light. When this is divided by the value at the same position of the locality correction table stored in advance. Then, $$g(x, \lambda) f(x, \lambda) / \sigma(\lambda) f(x, \lambda) = g(x, \lambda) / \sigma(\lambda)$$

which is in the proportional relation when a light source which is uniform in whole surface is used.

Figure 4:
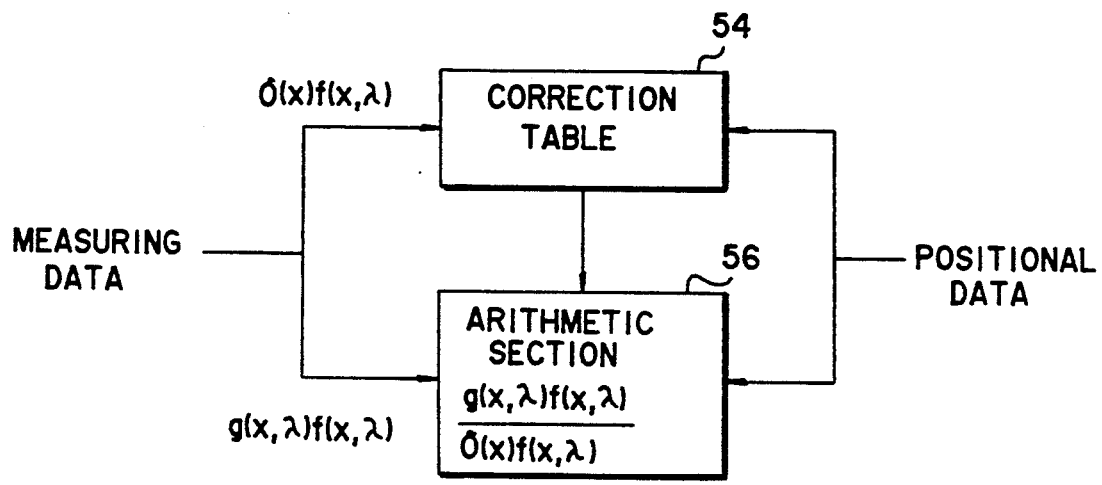
FIG. 4 is a block diagram showing the function of locality correction.

In order to carry out the locality correction, the CPU 50 performs the function of a correction table 54 and an arithmetic section 56, as shown in FIG. 4. Stored in the correction table 54 is the fluorescent measured value when the TLC plate with a fluorescent agent is mounted as the measuring plate. The arithmetic section 56 divides the fluorescent intensity when the specimen plate is measured by the value of the correction table at the same scanning position to obtain the locality-corrected fluorescent intensity.

Positional data in the scanning direction used in the correction table 54 and the arithmetic section 5 are obtained within the CPU 50 from data for controlling the stepping motor 26.

Figure 5:
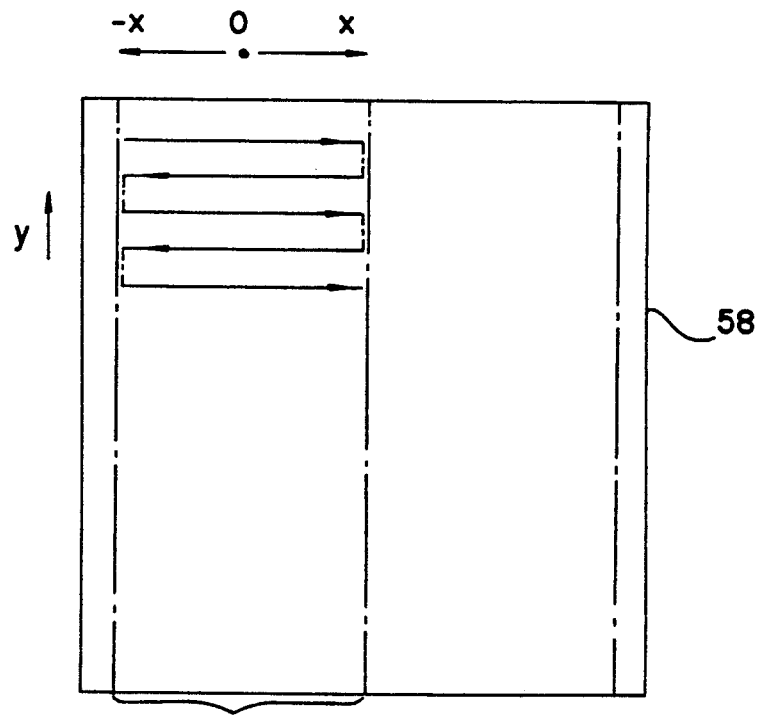
FIG. 5 is a view showing the scanning of flying spot system.

An example of scanning the excitation light of flying spot system is shown in FIG. 5.

Excitation light is scanned in the x direction with a TLC plate 58 fixed. Assume now that fluorescent measurement is carried out with 51 points in one scanning. The 26th point is the center point of the scanning. Scanning is repeatedly carried out in a zigzag manner such that the TLC plate 58 is moved by a predetermined distance in the y direction, scanning is then carried out in the -x direction and thereafter the TLC plate 58 is again moved in the y direction by a predetermined distance. Scanning is carried out over the whole surface of the TLC plate 58.

Stored in the locality correction table 54 are, as corrected data, positional data in the x direction and the fluorescent intensity of the TLC plate with a fluorescent agent with respect to one scanning in the x direction.

Figure 6:
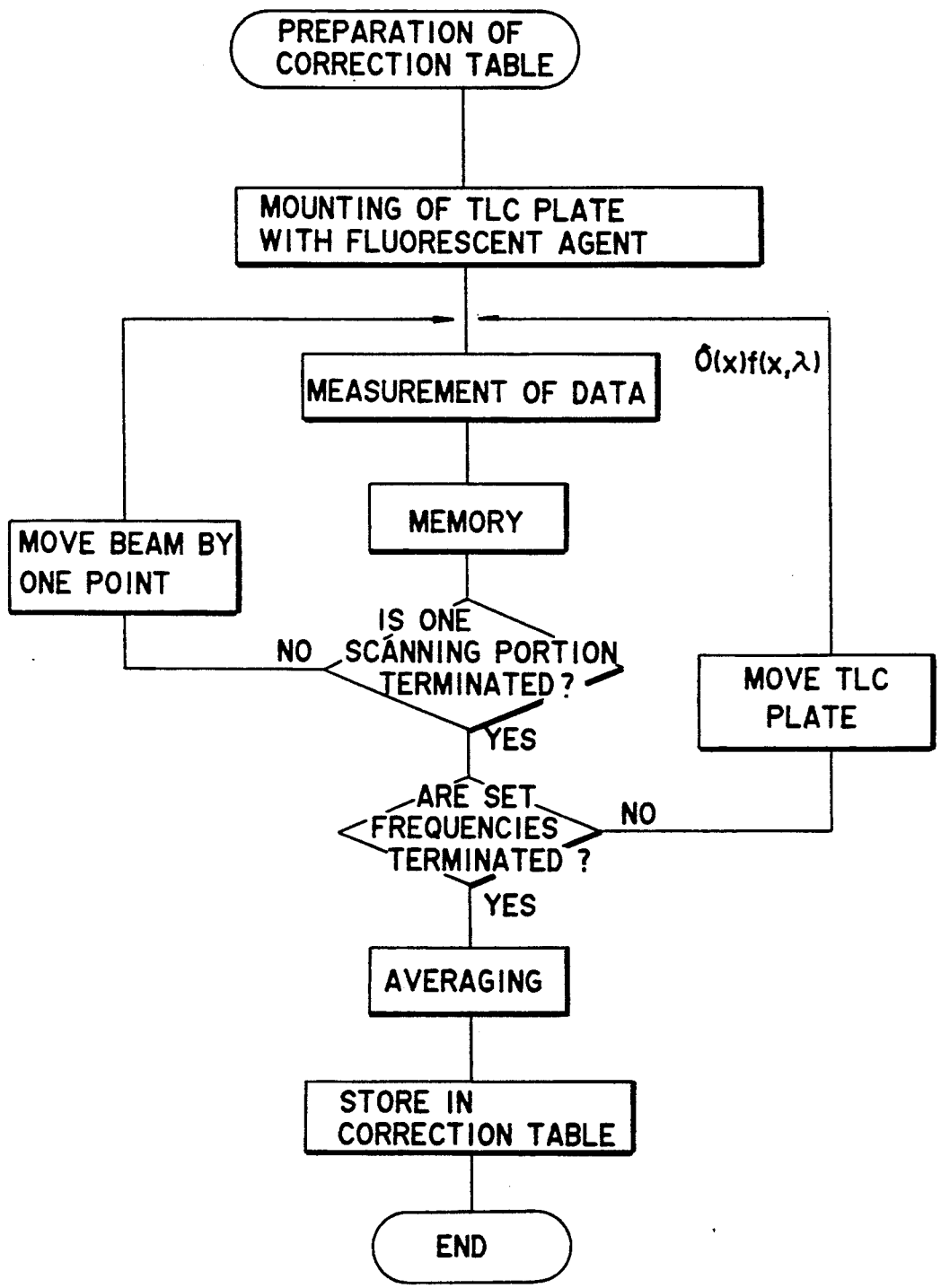
FIG. 6 is a flow chart showing the procedure for preparing a correction table.

FIG. 6 shows the procedure for preparing a correction table.

A TLC plate with a fluorescent agent is mounted at the position of the measuring plate. Excitation light is scanned in the x direction to measure data, whose value is stored. This procedure is carried out till one scanning is terminated. Then, the TLC plate is moved, and excitation light is likewise scanned to measure data. After the aforesaid procedure has been repeatedly carried out by set frequencies, the measured data is averaged every x coordinate, and the average value thereof is stored in the correction table.

FIG. 7 shows the measuring procedure.

A specimen TLC plate is mounted as the measuring plate. Data are measured while scanning, and the corrected value at the same position is called from the correction table to effect division. This procedure is repeated till one scanning is terminated. When one scanning is terminated, the specimen TLC plate is moved in the y direction by a predetermined one step, at which y position, measurement and division are repeated while scanning excitation light again.

When measurement of one line portion in the y direction is terminated, the specimen TLC plate is moved in the x direction, and the zigzag scanning is again carried out to repeat measurement and division.

As fluorescent data stored in the correction table, use can be made of data of relative value with a central position in the range of scanning excitation light in the x direction as a reference. The fluorescent measured value of the TLC plate with a fluorescent agent at the central position of scanning in the x direction is σ(λ) f (0, λ). The fluorescent measured value σ(λ) f (x, λ) at a suitable point is divided by the fluorescent measured value at the central point to obtain $$\sigma(\lambda) f(x, \lambda) / \sigma(\lambda) f(0, \lambda) = f(x, \lambda) / f(0, \lambda)$$

This value is stored as corrected data in the correction table. This case corresponds to that of assuming that no locality is present in the central portion. The obtained signal is convenience in processing data because it is matched in unit to the fluorescent measured value g (0, λ) f (0, λ) at the central point of scanning in the X direction of the specimen TLC plate.

According to the present invention, fluorescent data when a plate uniformed applied with a fluorescent agent within the range of scanning luminous flux is used as a correction value, and a fluorescent measured value when an actual specimen plate is measured is divided to effect locality correction. Therefore, in the densitometry of flying spot system, a fluorescent densitometry for fluorescent labelling a specimen to measure fluorescence for measurement with high sensitivity can be realized eliminating variation caused by position of data resulting from locality.

What is claimed is:

1. A fluorescent image densitometer of flying spot system, comprising:
   an excitation optical system for scanning and irradiating a measuring plate with an excitation light beam;

a fluorescence detection system for detecting a fluorescence from an excitation light irradiation position of the measuring plate;

a plate uniformly applied with a fluorescent agent at least within a range of excitation light;

a correction table for storing fluorescent data, measured with said plate mounted as the measuring plate, together with information of a position in a scanning direction on the measuring plate; and an arithmetic section for dividing fluorescence detection data measured with a specimen plate mounted as the measuring plate by fluorescent data at the same position in the scanning direction on the measuring plate stored in said correction table.

2. The fluorescent image densitometer according to claim 1, wherein the correction table for correcting a locality is prepared by measuring a TLC plate (thin film chromatography plate) with a fluorescent agent.

3. The fluorescent image densitometer according to claim 1, wherein the arithmetic section divides a fluorescent intensity when the specimen plate is measured by the value of the correction table at the same scanning position to obtain a locality-corrected fluorescent intensity.

* * * * *